(12) United States Patent
Provencher et al.

(10) Patent No.: US 9,877,712 B2
(45) Date of Patent: Jan. 30, 2018

(54) METHOD AND APPARATUS FOR PLACING A CANNULA OVER A STANDARD SWITCHING STICK

(71) Applicant: Arthrex, Inc., Naples, FL (US)

(72) Inventors: Matthew T. Provencher, Weston, MA (US); Kyle Anderson, West Bloomfield, MI (US); Peter J. Dreyfuss, Naples, FL (US); Brian S. Cohen, Dublin, OH (US)

(73) Assignee: Arthrex, Inc., Naples, FL (US)

( * ) Notice: Subject to any disclaimer, the term of this patent is extended or adjusted under 35 U.S.C. 154(b) by 428 days.

(21) Appl. No.: 14/560,728

(22) Filed: Dec. 4, 2014

(65) Prior Publication Data

US 2015/0150594 A1  Jun. 4, 2015

Related U.S. Application Data

(60) Provisional application No. 61/911,512, filed on Dec. 4, 2013.

(51) Int. Cl.
*A61B 17/34* (2006.01)
*A61B 17/02* (2006.01)
*A61B 17/00* (2006.01)

(52) U.S. Cl.
CPC ...... *A61B 17/0218* (2013.01); *A61B 17/3417* (2013.01); *A61B 17/3421* (2013.01); *A61B 2017/0046* (2013.01); *A61B 2017/00469* (2013.01)

(58) Field of Classification Search
CPC ..... A61B 17/34; A61B 17/02; A61B 17/3415; A61B 17/0218; A61B 17/3423
See application file for complete search history.

(56) References Cited

U.S. PATENT DOCUMENTS

| | | | | |
|---|---|---|---|---|
| 2008/0242930 A1* | 10/2008 | Hanypsiak | ......... | A61B 17/3421 600/114 |
| 2014/0296647 A1* | 10/2014 | Kucklick | ........... | A61B 17/3423 600/204 |

* cited by examiner

*Primary Examiner* — Christopher Beccia
(74) *Attorney, Agent, or Firm* — Rubin and Rudman LLP

(57) ABSTRACT

Cannula assemblies and methods of conducting surgeries. The cannula assembly comprises a cannula that is sized for the common 4 mm arthroscopy switching stick, which is put in a one-step fashion with the use of a unique switching stick inserter. All steps for placement of the cannula are performed in a single forward motion, i.e., no backing up of components are necessary for placement. The method of conducting surgery includes the steps of: providing a cannula/switching stick assembly comprising a cannula sized to accommodate a corresponding switching stick, and a switching stick inserter (modular handle) designed to fit on the switching stick, and to help insert and control the switching stick; and inserting the cannula/switching stick assembly through an arthroscopic portal during a surgical procedure, in a single forward motion.

7 Claims, 1 Drawing Sheet

METHOD AND APPARATUS FOR PLACING A CANNULA OVER A STANDARD SWITCHING STICK

CROSS-REFERENCE TO RELATED APPLICATIONS

This application claims the benefit of U.S. Provisional Application No. 61/911,512, filed Dec. 4, 2013, the entire disclosure of which is incorporated by reference herein.

FIELD OF THE INVENTION

The present invention relates to methods and apparatus for surgical procedures.

BACKGROUND OF THE INVENTION

Cannulas are often inserted into various portals such as arthroscopic portals to provide a convenient passageway through which various instruments may pass. Current cannulas are typically provided with a reusable cannulated obturator which is inserted over (goes over) a switching stick prior to cannula insertion. The cannulated obturator and switching stick are typically used to enlarge the size of the arthroscopic portal to allow access of additional instruments such as cannulas.

There is a need for improved efficiency and size of cannulas that are used in arthroscopic procedures. A method of placing a cannula over a standard switching stick without the need of the surgeon to remove his/her hand from the switching stick inserter is also needed.

SUMMARY OF THE INVENTION

The present invention provides a cannula/switching stick assembly and a method of placing a cannula over a standard switching stick.

The present invention provides a cannula that is sized for the common 4 mm arthroscopy switching stick, which is put in a one step fashion with the use of a unique switching stick inserter. All steps for placement of the cannula are performed in a single forward motion, i.e., no backing up of components are necessary for placement.

The present invention also provides methods of conducting arthroscopic surgery by: (i) providing a cannula/switching stick assembly comprising a cannula sized to accommodate a corresponding switching stick, and a switching stick inserter (modular handle) designed to fit on the switching stick, and to help insert and control the switching stick; and (ii) inserting the cannula/switching stick assembly through an arthroscopic portal during a surgical procedure, in a single forward motion.

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENTS

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides a cannula/switching stick assembly and a method of placing a cannula over a standard switching stick.

Figure 1:
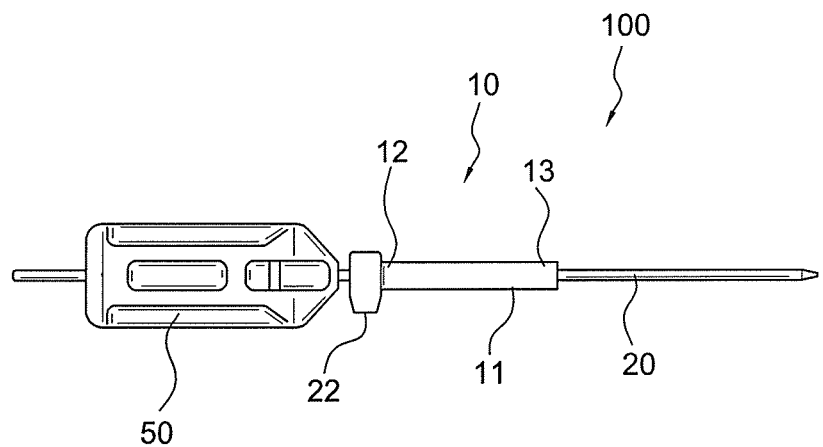
FIG. 1 shows a cannula/switching stick assembly of the present invention (comprising a cannula, a switching stick and a switching stick inserter/handle).

Referring now to the drawings, where like elements are designated by like reference numerals, FIG. 1 illustrates an exemplary embodiment of cannula assembly 100 of the present invention. Assembly 100 includes cannula 10 (for example, a 4 mm cannula 10) that is inserted over a switching stick 20 (for example, a 4 mm switching stick 20). Assembly 100 also includes a switching stick inserter or handle 50 provided at the proximal end of the assembly and designed to securely engage a most proximal end of the switching stick 20. Preferably, switching stick inserter/handle 50 is modular and sized to fit on the switching stick 20. The switching stick inserter/handle 50 helps insert and control the switching stick 20 during surgery. The switching stick inserter/handle 50 is fully cannulated in the exemplary embodiment shown in FIG. 1.

Cannula 10 comprises an elongated body 11 (cannulated shaft 11) having a proximal end 12 and a distal end 13. The elongated body 11 of cannula 10 is slidably moveable relative to the switching stick 20. Preferably, the switching stick 20 has an outer diameter about equal to an inner diameter of cannulated shaft 11 of the cannula. Cannula 10 is an arthroscopic cannula which may be formed of various materials, for example, metals such as stainless steel (in the shape of a stainless steel tubing), polymers such as translucent polymer, or other known biocompatible materials, alloys or compositions known in the art.

The elongated body 11 of cannula 10 may be also provided with a plurality of threads. The optional threads may be provided on the whole length of the elongated body 11 or, alternatively, on at least a length of the body 11.

An outflow/inflow port 22 is provided at the proximal end 13 of the body 11 of cannula 10. The outflow/inflow port 22 may be a fluid passage with various configurations and cross-sections, for example, a tubular configuration. The outflow/inflow port 22 may be connected to a source of fluid or irrigation solution, gas, or vacuum, for supplying irrigation or gas through the cannula to the work site during the arthroscopic procedure. If desired, a sealing means, such as a plastic cap, for example, may be optionally employed to securely engage the distal end of the outflow/inflow port 22 when the cannula is not attached to the switching stick.

An exemplary method of conducting surgery comprises inter alia the steps of (i) providing a cannula/switching stick assembly 100 comprising cannula 10, switching stick 20, and switching stick inserter/handle 50; and (ii) inserting the cannula/switching stick assembly 100 into an arthroscopic portal in a single, one-step forward motion, during a surgical procedure.

Another exemplary method of conducting arthroscopic surgery comprises inter alia the steps of: (i) providing an incision in tissue at a joint location; (ii) placing a cannula 10 over a switching stick 20; (iii) subsequently, attaching an inserter 50 to the switching stick 20; and (iv) inserting the switching stick 20 and the cannula 10 through the incision, by using the inserter 50 and pushing the switching stick 20 and the cannula 10 in a single-step forward movement, and without backing out the switching stick 20 from the incision.

Figure 2:
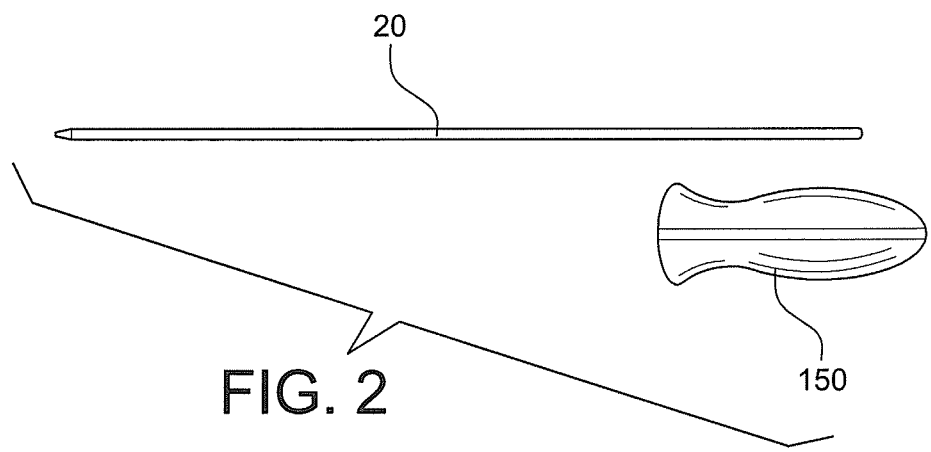
FIG. 2 shows a switching stick and a corresponding switching stick inserter/handle according to another exemplary embodiment of the present invention.

FIG. 2 illustrates a switching stick 20 and a corresponding switching stick inserter/handle 150 according to another exemplary embodiment of the present invention.

Prior art cannulas typically utilize a reusable cannulated obturator that goes over the switching stick as a second or third step. The inventive system/assembly 100 of the present invention allows the surgeon to place the cannula without removing the surgeon's hand from the switching stick inserter. In this manner, the efficiency of the overall arthroscopic surgery is improved as well as the size of the cannula. The cannula is sized for a standard 4 mm arthroscopy switching stick, which is put in a one-step fashion with the use of a unique switching stick inserter. All steps for placement of the cannula are performed in a single forward motion, i.e., no backing up of components is necessary for placement.

Although the assembly 100 of the invention can be used in large body cavities such as the abdomen, it is particularly useful in smaller cavities such as joints (i.e., knees, shoulders, elbows, ankles, and the like). During arthroscopic surgery of a joint, the joint is typically inflated with water as opposed to a gas which is typically used in abdominal surgical procedures as the surgical procedures performed within a joint are significantly different from those performed within an abdominal cavity. Employing assembly 100 of the present invention in arthroscopic surgeries of joints provides a low-cost, efficient and simple method for placing the cannula and switching stick within the portal, without removing the surgeon's hand from the switching stick inserter. In this manner, the surgeon is not required to do a truly manual second step, i.e., the surgeon would not need to load the cannula onto the switching stick after the switching stick is inserted in the joint space.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed is:

1. A method of placing a cannula over a switching stick during an arthroscopic surgery to form a switching stick/cannula assembly, comprising the steps of:
   connecting a switching stick inserter to a switching stick;
   sliding a cannula over the switching stick in a single forward motion without the use of an obturator; and
   inserting the switching stick/cannula assembly into a joint space in a single forward motion and without backing up the switching stick from the joint space.

2. The method of claim 1, wherein the switching stick inserter is a modular handle.

3. The method of claim 1, wherein the switching stick has an outer diameter about equal to an inner diameter of a cannulated shaft of the cannula.

4. A method of conducting arthroscopic surgery, comprising the steps of:
   providing an incision in tissue at a joint location;
   placing a cannula over a switching stick;
   subsequently, attaching an inserter to the switching stick; and
   inserting the switching stick and the cannula through the incision, by using the inserter and pushing the switching stick and the cannula in a single-step forward movement, and without backing out the switching stick from the incision.

5. The method of claim 4, wherein the switching stick has an outer diameter about equal to an inner diameter of an elongated cannulated shaft of the cannula.

6. The method of claim 4, wherein the inserter is a hand-held instrument.

7. The method of claim 4, wherein the cannula is designed to be removably attached to the switching stick.

* * * * *